(12) United States Patent
Ciccarelli et al.

(10) Patent No.: US 6,383,512 B1
(45) Date of Patent: May 7, 2002

(54) VESICULAR COMPLEXES AND METHODS OF MAKING AND USING THE SAME

(75) Inventors: Richard B. Ciccarelli, Yorktown Heights, NY (US); C. Satishchandran; Catherine J. Pachuk, both of Lansdale, PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/542,409

(22) Filed: Apr. 4, 2000

Related U.S. Application Data

(62) Division of application No. 09/402,507, filed as application No. PCT/US98/08799 on Apr. 30, 1998.
(60) Provisional application No. 60/045,122, filed on Apr. 30, 1997.

(51) Int. Cl.$^7$ ................................................. A61K 9/127
(52) U.S. Cl. ...................... 424/450; 435/69.1; 435/375; 514/44
(58) Field of Search .......................... 424/450; 435/459, 435/69.1, 375; 514/44

(56) References Cited

U.S. PATENT DOCUMENTS

| | | | |
|---|---|---|---|
| 4,945,050 A | 7/1990 | Sanford et al. | 435/440 |
| 5,514,788 A | 5/1996 | Bennett et al. | 536/23.1 |
| 5,593,972 A | 1/1997 | Weiner et al. | 514/44 |
| 5,948,441 A | 9/1999 | Lenk et al. | 424/489 |

OTHER PUBLICATIONS

Leslie Coney et al, "Facilitated DNA Inoculation Induces Anti–HIV–1 Immunity in vivo", Vaccine, 12(16):1545–1550 (Dec., 1994).

Heather Davis et al, "Use of Plasmid DNA for Direct Gene Transfer and Immunization", Annals of the New York Academy of Sciences, 772:21–29, Margaret A. Liu ed., The New York Academy of Sciences, New York, New York (1995).

Catherine Pachuk et al, "Characterization of a New Class of DNA Delivery Complexes Formed by the Local Anesthetic Bupivacaine", Biochimica et Biophysica Acta, 1468:20–30 (2000).

David Bernstein et al, "Effects of DNA Immunization Formulated with Bupivacaine in Murine and Guinea Pig Models of Genital Herpes Simplex Virus Infection", Vaccine, 17:1964–1969 (1999).

E. De–Paula and S. Schreier, "Molecular and Physicochemical Aspects of Local Anesthetic–Membrane Interaction", Braz. J. Med. Biol. Res., 29:877–894 (Jul. 1996).

J. O. Rädler, et al. "Structure of Dna–Cationic Liposome Complexes: DNA Intercalation in Multilamellar Membranes in Distinct Interhelical Packing Regimes", Science, 275:810–814 (Feb. 7, 1997).

P. Schieper and R. Steiner "The Effect of Different Surface Chemical Groups on Drug Binding to Liposomes", Chemistry and Physics of Lipids, 34: 81–92 (Dec. 1983).

G. Strichartz et al., "Fundamental Properties of Local Anesthetics. II. Measured Octanol:Buffer Partition coefficients and pKa Values of Clinically Used Drugs", Anesth. Analg., 71:158–170 (Aug. 1990).

Orkin et al., Report and Recommendations of the Panel to Access the NIH Investment in Research on Gene Therapy, 1995, NIH, Bethesda, MD, Dec. 2, 1995.*

French Anderson et al., Nature, vol. 392, 1998, pp. 25–30, Apr. 30, 1998.*

Editorial, Nature Biotechnology, vol. 15, 1997, p. 815, Sep. 1997.*

Verma et al., Nature, vol. 389, 1997, pp. 239–242, Sep. 18, 1997.*

* cited by examiner

Primary Examiner—James Ketter
(74) Attorney, Agent, or Firm—Howson and Howson

(57) ABSTRACT

Composition comprising lamellar vesicles that comprise a local anesthetic and a nucleic acid molecule are disclosed. Methods of making such compositions are disclosed. Method of delivering proteins to cells of individuals are disclosed. Methods of inducing immune responses in individuals are disclosed. Methods of delivering nucleic acid molecules to cells of individuals are disclosed.

51 Claims, No Drawings

VESICULAR COMPLEXES AND METHODS OF MAKING AND USING THE SAME

This is a divisional of U.S. patent application Ser. No. 09/402,507, filed Oct. 5, 1999, which is a 371 of PCT/US98/08799, filed Apr. 30, 1998, which claims the benefit of the priority of U.S. Provisional Patent Application No. 60/045,122, filed Apr. 30, 1997.

FIELD OF THE INVENTION

The present invention relates to molecular complexes which include local anesthetics, to pharmaceutical compositions comprising the same, and to methods of making and using the same.

BACKGROUND OF THE INVENTION

Local anaesthetics are a large group of compounds which include several classes of compounds. Physiologically active natural or synthetic chemicals or biologicals and their derivatives act at/in cell membranes and/or specific receptor molecules at/in cell membranes in vivo or in vitro. Local anesthetics are described in De-Paula, E. And S. Schreier (1996) Braz. J. Med. Res. 29:877–894 and Ritchie, J. M. and N. M. Greene "Local Anesthetics", Chapter 15 302–321, which are both incorporated herein by reference, describe local anesthetics and their uses.

In addition, the use of local anesthetics in combination with nucleic acid molecules for in vivo gene transfer generally and in particular for protective and therapeutic vaccination protocols as well as gene therapy and antisense protocols is described in U.S. Pat. No. 5,593,972 issued on Jan. 14, 1997 to Weiner et al. and in PCT application PCT/US94/00899, which are both incorporated herein by reference. This application claims priority to U.S. Provisional Application No. 60/045,122 filed Apr. 30, 1997, which is incorporated herein by reference.

SUMMARY OF THE INVENTION

The present invention relates to compositions that comprise lamellar vesicles that comprise a local anesthetic and a nucleic acid molecule. In some embodiments, the proportion of local anesthetic to nucleic acid in the vesicles is 0.01–2.5% weight to volume (w/v) local anesthetic to 1 µg/ml–10 mg/ml nucleic acid. In some embodiments, the proportion of local anesthetic to nucleic acid in the vesicles is 0.05–1.25% (w/v) local anesthetic to 100 µg/ml–1 mg/ml nucleic acid. In some embodiments, the proportion of local anesthetic to nucleic acid in the vesicles is 0.1–0.5% (w/v) local anesthetic to 500 µg/ml–1500 µg/ml nucleic acid. In some embodiments, the lamellar vesicles up to about 200 nm diameter as measured by scanning electron microscopy. In some embodiments, the lamellar vesicles are 50–150 nm diameter as measured by scanning electron microscopy. In some embodiments, greater than 50% of said lamellar vesicles greater that 300 nm diameter as measured by scanning electron microscopy. In some embodiments, greater than 50% of said lamellar vesicles are less than 400 nm diameter as measured by scanning electron microscopy. In some embodiments, the local anesthetic is bupivacaine, etidocaine, tetracaine, procainamide, chloroprocaine, ropivacaine, prylocaine, mepivacaine, lidocaine, procaine, carbocaine, methyl bupivacaine or cocaine. In some embodiments, the nucleic acid is DNA. In some embodiments, the nucleic acid is plasmid DNA. In some embodiments, the lamellar vesicles further comprise one or more compounds selected from the group consisting of: cationic lipids, neutral lipids, anionic lipids, cationic surfactants, neutral surfactants, anionic surfactants, cationic detergents, neutral detergents, and anionic detergents. In some embodiments, the lamellar vesicles further comprise one or more compounds selected from the group consisting of: proteins, polypeptides, peptides, and non-proteinaceous drugsltherapeutic compounds. In some embodiments, the nucleic acid is DNA comprising a DNA sequence that encodes an immunogen.

The present invention further relates to methods of preparing compositions that comprise lamellar vesicles. The methods comprise the step of forming the lamellar vesicles by combining 0.01–2.5% (w/v) local anesthetic with 1 µg/ml–10 mg/ml nucleic acid in the presence of 0–2M salt at a pH of 4–8.5. In some embodiments, the lamellar vesicles are formed by combining 0.05–1.25% (w/v) local anesthetic with 100 µg/ml–1mg/ml nucleic acid in the presence of 0–500 mM salt at a pH of 6–7.5. In some embodiments, the lamellar vesicles are formed by combining 0.1–0.5% (w/v) local anesthetic with 500 µg/ml–1500 µg/ml nucleic acid in the presence of 0–500 mM salt at a pH of 6–7.5. In some embodiments, the lamellar vesicles are formed by combining 0.1–0.5% (w/v) local anesthetic with 500 µg/ml–1500 µg/ml nucleic acid in the presence of greater than 2M salt at a pH of 6–7.5 followed by removal of salt to below 500 mM. In some embodiments, proteins, polypeptides, peptides, or non-proteinaceous drugs/therapeutic compounds are also combined with the local anesthetic and nucleic acid to produce lamellar vesicles that include the proteins, polypeptides, peptides, or non-proteinaceous drugs/therapeutic compounds.

The present invention further relates to a method of delivering a protein, which includes polypeptides and peptides, to a cell of an individual. The method comprises the step of administering to the individual a composition that comprises lamellar vesicles that comprise a local anesthetic and a nucleic acid molecule. The lamellar vesicles comprise nucleic acid molecules that comprise a nucleotide sequence that encodes the protein operably linked to regulatory sequences. The nucleic acid molecules are taken up by cells of the individual and expressed to produce the protein.

The present invention further relates to a method of delivering a protein, polypeptide, peptide, non-proteinaceous drug/therapeutic compound, intact viral particle or fragment thereof, or microorganism to a cell of an individual. The method comprises the step of administering to the individual a composition that comprises lamellar vesicles that comprise a local anesthetic, a nucleic acid molecule and the protein, polypeptide, peptide, or non-proteinaceous drug/therapeutic compound.

The present invention further relates to a method of inducing an immune response in an individual. The method comprises the step of administering to the individual a composition that comprises lamellar vesicles that comprise a local anesthetic and a nucleic acid molecule. The lamellar vesicles comprise nucleic acid molecules that comprise a nucleotide sequence that encodes an immunogen operably linked to regulatory sequences. The nucleic acid molecules are taken up by cells of the individual, expressed to produce the immunogen and an immune response is generated against the immunogen by the individual. In some embodiments, the lamellar vesicles further comprise an immunogenic protein or peptide. In some embodiments, lamellar vesicles further comprise a physiologically active protein.

The present invention further relates to a method of delivering a nucleic acid molecule to a cell of an individual.

The method comprises the step of administering to the individual a composition that comprises lamellar vesicles that comprise a local anesthetic and a nucleic acid molecule. The lamellar vesicles comprise nucleic acid molecules that comprises a nucleotide sequence that encodes said protein operably linked to regulatory sequences, an antisense oligonucleotide, a ribozyme or a triplex forming nucleic acid molecule.

DETAILED DESCRIPTION OF THE INVENTION

The present invention provides lamellar vesicles which comprise local anesthetics and nucleic acid molecules. Such lamellar vesicles are formed spontaneously when solutions of local anesthetics and nucleic acid molecules are combined in specific proportions under specific chemical conditions. The vesicles can include additional compounds known for their membrane forming properties such as lipids, surfactants and detergents. Moreover, additional compounds such as proteins, polypeptides, peptides, or non-proteinaceous drugs/therapeutic compounds can be encapsulated within the vesicles.

The lamellar vesicles of the invention are useful to deliver materials to cells in vitro and in vivo. Such materials include nucleic acid molecules as well as proteins, polypeptides, peptides, and non-proteinaceous drugs/therapeutic compounds. According to some embodiments, the present invention provides methods of delivering nucleic acids and/or proteins, polypeptides, peptides, and/or non-proteinaceous drugs/therapeutic compounds to cells of an individual.

According to some embodiments, the present invention provides methods of delivering nucleic acid molecules that encode proteins to cells of an individual wherein the nucleic acid sequence that encodes the protein of the nucleic acid molecules is expressed in order to deliver the protein to such cells in vivo.

According to some embodiments, the present invention provides methods of delivering nucleic acid molecules that encode immunogenic proteins to cells of an individual wherein the nucleic acid sequence that encodes the immunogenic protein of the nucleic acid molecules is expressed in order to deliver the immunogenic protein to such cells, wherein an immune response against the immunogenic protein is induced in the individual. In some embodiments, nucleic acid molecules also encode immunomodulating proteins wherein the nucleic acid sequence that encodes the immunomodulating proteins is expressed in order to deliver the immunomodulating proteins to the individual and effect, enhance or otherwise modulate the immune response induced against the immunogenic protein. In some embodiments, the lamellar vesicles further comprise one or more immunomodulating proteins, polypeptides, peptides, or non-proteinaceous drugs/therapeutic compounds in order to deliver the immunomodulating proteins, polypeptides, peptides, or non-proteinaceous drugs/therapeutic compounds to the individual in order to effect, enhance or otherwise modulate the immune response induced against the immunogenic protein. In some embodiments, the lamellar vesicles further comprise one or more immunogenic proteins and/or peptides in order to deliver the immunogenic proteins or peptides to the individual to provide additional targets against which an immune response can be induced. In some embodiments, the immunogenic protein or peptide is identical or related to the immunogenic protein encoded by the nucleic acid molecules.

According to some embodiments, the present invention provides methods of delivering nucleic acid molecules that encode non-immunogenic therapeutically effective proteins to cells of an individual wherein the nucleic acid sequence that encodes the non-immunogenic therapeutically effective protein of the nucleic acid molecules is expressed in order to deliver the non-immunogenic therapeutically effective protein to such cells, wherein the non-immunogenic therapeutically effective provides a desired physiological effect on the individual. In some embodiments, the nucleic acid molecules encode immunomodulating proteins as discussed above. In some embodiments, the lamellar vesicles further comprise one or more proteins, polypeptides, peptides, or non-proteinaceous drugs/therapeutic compounds in order to deliver the proteins, polypeptides, peptides, or non-proteinaceous drugs/therapeutic compounds to the individual in conjunction with the delivery of the protein encoded by the nucleic acid sequence on the nucleic acid molecules.

According to some embodiments, the present invention provides methods of delivering nucleic acid molecules that are antisense, ribozyme or triplex forming nucleic acid molecules.

According to some embodiments, the present invention provides methods of delivering proteins, polypeptides, peptides, and/or non-proteinaceous drugs/therapeutic compounds to cells of an individual wherein the lamellar vesicles are used as a vehicle/carrier to facilitate delivery of such proteins, polypeptides, peptides, and/or non-proteinaceous drugs/therapeutic compounds and to protect the same from degradation during the delivery process.

According to the present invention, the use of local anesthetics in gene transfer methods such as those described in U.S. Pat. No. 5,593,972 and PCT/US94/00899 are improved using vesicular compositions comprising local anesthetics and nucleic acid molecules. The vesicular compositions are formed when local anesthetics and nucleic acid molecules are combined under conditions which favor assembly of vesicular structures. The vesicular compositions provide improved gene transfer and thus improved methods of immunization, gene therapy and antisense and ribozyme administration. Moreover, the vesicles can be used and adapted to co-deliver proteins, polypeptides, peptides, and/or non-proteinaceous drugs/therapeutic compounds together with the nucleic acid molecules that encode the genes to be transferred. Alternatively, nucleic acid molecules can be used exclusively as carrier nucleic acid molecules, i.e. nucleic acid molecules that are not transcribed or translated, to form vesicles that encapsulate and which can be used as improved delivery vehicles for proteins, polypeptides, peptides, and/or non-proteinaceous drugs/therapeutic compounds. Accordingly, vesicular compositions comprising local anesthetics, nucleic acid molecules and other types of therapeutic or immunogenic materials such as drugs, hormones and immunogens may also be prepared and used according to the present invention.

Local anesthetics are highly lipophilic/hydrophobic molecules which typically, but not always, contain a tertiary nitrogen on one end of the molecule which can carry positive charge as a protonated species. This occurs in aqueous solutions at or below the pKa of the nitrogen (typically pKa=7–9 range for most local anesthetics). Therefore, local anesthetics have the property of being extremely hydrophobic as a neutral species (above pKa) and of being charge-polarized (i.e. having a positive charged end and a hydrophobic end) at or below the pKa. As used herein, the term "local anesthetic" is intended to refer to those local anesthetics useful to make lamellar vesicles according to the invention. Thus, the term "local anesthetic" as used herein refers to those local anesthetics that contain a cationic nitrogen, have a pKa of about 7–9, bind to DNA and contain a hydrophobic group.

Local anesthetics typically have an internal amide link (amide-type local anesthetics) or an internal ester link (ester-type local anesthetics). Examples of amide-type local anesthetics include bupivacaine, lidocaine, and etidocaine; examples of ester-type local anesthetics include procaine and tetracaine. Benzocaine is an example of an ester-type local anesthetic which does not have a tertiary nitrogen end. Examples of local anesthetic structures are set out in: PCT/US94/00899; De-Paula, E. and S. Schreier, Supra; Ritchie, J. M. and N. M. Greene, Supra; and Strichartz et al. (1990), Anesth. Analg., 71:158–170, which is incorporated herein by reference.

Local anesthetics have the property of partitioning from aqueous solutions into the organic phase as neutral or charged species (Strichartz et al. Supra and Schlieper P. and Steiner, R. (1983) Chemistry and Physics of Lipids, 34:81–92, which is incorporated herein by reference.). Bupivacaine is an example of an local anesthetic which can partition into n-octanol as both the charged and neutral species. Local anesthetics have been reported to partition into lipids, mixtures of lipids, and into liposomes.

In vivo, amide-type local anesthetics have a longer biological half-life since they are not degraded as rapidly in blood as ester-type local anesthetics and are typically associated with serum proteins, particularly alpha-1-glycoprotein, resulting in a depot effect. Amide-type local anesthetics are slowly degraded by liver. Ester-type local anesthetics are rapidly degraded in blood or tissue by a serum esterase.

The cationic charged end of the local anesthetic binds to anionic groups on nucleic acid molecules at a pH below the pKa of the amine, for example at physiological pH. The local anesthetics-nucleic acid complex becomes more charge neutral, hydrophobic and lipophilic under these conditions and can partition into/through the lipid membrane of cells, delivering the nucleic acid to the cell. Local anesthetics have been shown to have higher lipid partition coefficients as a neutral species.

Lamellar vesicles of some embodiments of the invention include one or more local anesthetics selected from the group consisting of: bupivacaine, etidocaine, tetracaine, procainamide, chloroprocaine, ropivacaine, prylocaine, mepivacaine, lidocaine, procaine, carbocaine, methyl bupivacaine and cocaine. In some embodiments, lamellar vesicles include a single species of local anesthetic, including racemic mixtures and pure isomers thereof. In some embodiments, lamellar vesicles include two or more different species of local anesthetic.

In some preferred embodiments of the invention, one or more different cationic hydrophobic local anesthetics form vesicle structures by complexing with nucleic acid molecules. The vesicular membrane formed by local anesthetic or local anesthetics may include "co-agent" lipid, detergent and/or surfactant amphiphile molecules. The vesicles may, in some embodiments, further entrap "other agents" or "active agents" which associate with the vesicular complex forming compounds. Such other active agents include proteins, polypeptides, peptides, or non-proteinaceous drugs/therapeutic compounds. Due to the highly apolar nature of the cationic amphiphile local anesthetics, the local anesthetics alone or in combination with other compounds such as lipids, amphiphiles, lipophilic/hydrophobic compounds, surfactants, detergents and/or lipid soluble vitamins such as vitamins A, D and K (referred to herein as "co-agents") can form self-assembly structures including lamellae sheets and vesicles when combined with nucleic acid molecules. Radler, J. O. et al, (1997) Science 275, 810–814, which is incorporated herein by reference, discusses lipid self-assembly structures. Such structures might be further stabilized by strong intra-molecule hydrophobic stacking-type interactions, for example between the aromatic groups. In some embodiments of the present invention, local anesthetics are used together with one or more lipids, amphiphiles, lipophilic/hydrophobic compounds, surfactants, and/or detergents, particularly cationic or neutral lipids, cationic or neutral amphiphiles, cationic or neutral lipophilic/hydrophobic compounds, cationic or neutral surfactants, and/or cationic or neutral detergents to form lamellar vesicles which include nucleic acid molecules.

Due to the apolar nature of the cationic local anesthetics species, mixtures of local anesthetics with co-agents are used to form larger self-assembly structures in combination with nucleic acid molecules. Mixtures of single or combinations of local anesthetics are mixed with cationic, neutral, or anionic lipids, and nucleic acid molecules to form liposome-like structures. Vesicles can be formed using one or more local anesthetics with a combination of one or more compounds selected from cationic, neutral, or anionic lipids, cationic, neutral, or anionic amphiphiles, cationic, neutral, or anionic lipophilic/hydrophobic compounds, cationic, neutral, or anionic surfactants, and/or cationic, neutral, or anionic detergents. In one embodiment, a cationic local anesthetic such as bupivacaine is combined with a different cationic amphiphile such as a synthetic compound as DOTMA; or with a neutral synthetic compound such as DOPE and/or natural lipid such as cholesterol. In another embodiment, a cationic local anesthetic is combined with anionic and/or neutral lipids.

Lamellar vesicles according to the invention may be used to encapsulate active agents for delivery to tissues and cells. Therapeutic and/or immunogenic and/or imaging agents (referred to herein as "active agents"), including proteinaceous as well as non-proteinaceous compounds can be associated with or encapsulated within these lamellar structures for in vitro or in vivo delivery into tissues and cells. Active agent molecules include therapeutic and/or immunogenic proteins, polypeptides and peptides as well as non-proteinaceous drugs/therapeutic compounds. Other molecules can be associated with these structures to reduce their immunogenicity (such as PEG's) or to improve their ability to fuse to cells or disrupt endosomes within cells after their uptake (fusogenic -lipids, -peptides, -polymers).

In some embodiments of the invention, the nucleic acid molecules may be plasmid DNA genetic constructs which are DNA vaccines or gene therapy constructs that encode immunogens or biologically active, therapeutically desirable proteins wherein the coding sequences are operably linked to regulatory elements necessary for expression in cells in the individual to whom the vesicular complexes are administered (i.e. the DNA operably encodes the protein that is expressed). DNA constructs are described in U.S. Pat. No. 5,593,972 issued on Jan. 14, 1997 to Weiner et al. and in PCT application PCT/US94/00899. Importantly, if a coding sequence is to be transcribed and translated, it must be operably linked to regulatory elements which function in the cells into which the DNA molecule is delivered.

Some aspects of the present invention relate to methods of introducing genetic material into the cells of an individual in order to induce immune responses against proteins and peptides which are encoded by the genetic material. The methods comprise the steps of administering to the tissue of said individual, lamellar vesicles comprising local anesthetic and either a single species of nucleic acid molecule that comprises a nucleotide sequence that encodes one or more desired peptides or proteins including at least one immunogenic peptide or protein. Additionally, in some embodiments, nucleic acid molecules are provided which comprise a nucleotide sequence that encodes one or more immunomodulating protein. The nucleic acid molecule(s) may be provided as plasmid DNA. In some embodiments, the lamellar vesicles further comprise one or more immunomodulating proteins, polypeptides, peptides, or non-proteinaceous drugs/therapeutic compounds and/or one or more immunogenic proteins or peptides.

According to some aspects of the present invention, compositions and methods are provided which prophylactically and/or therapeutically immunize an individual against an allergen, pathogen or abnormal, disease-related cell. The genetic material that encodes an immunogen that can induce in immune response in the individual against an allergen, pathogen or abnormal cells.

The genetic material is expressed by the individual's cells and serves as an immunogenic target against which an immune response is elicited. The resulting immune response is broad based: in addition to a humoral immune response, both arms of the cellular immune response are elicited. The methods of the present invention are useful for conferring prophylactic and therapeutic immunity. Thus, a method of immunizing includes both methods of immunizing against immunogens and thus for example of protecting an individual from pathogen challenge, or occurrence or proliferation of specific cells as well as methods of treating an individual suffering from pathogen infection, hyperproliferative disease or autoimmune disease.

As used herein the terms "immunogen" and "target protein" are meant to refer to peptides and protein encoded by gene constructs of the present invention which act as target proteins for an immune response. The terms "target protein" and "immunogen" are used interchangeably and refer to a protein against which an immune response can be elicited. The target protein is an immunogenic protein which shares at least an epitope with an allergen or a protein from the pathogen or undesirable cell-type such as a cancer cell or a cell involved in autoimmune disease against which immunization is required. The immune response directed against the target protein will protect the individual against and treat the individual for the specific infection or disease with which the target protein is associated.

The present invention is useful to elicit broad immune responses against a target protein, i.e. proteins specifically associated with pathogens, allergens or the individual's own "abnormal" cells. The present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

Some aspects of the present invention relate to methods of introducing genetic material into the cells of an individual in order to deliver a non-immunogenic protein and peptide which are encoded by the genetic material to the individual. The methods comprise the steps of administering to the tissue of said individual, lamellar vesicles comprising local anesthetic and either a single species of nucleic acid molecule that comprises a nucleotide sequence that encodes one or more desired non-immunogenic, biologically active peptides, polypeptides or proteins which have a non-immunogenic physiological effect on the individual. As used herein, the term "physiologically active protein" is intended to refer to biologically active peptides, polypeptides or proteins which have a non-immunogenic physiological effect on the individual. In some embodiments, nucleic acid molecules are provided which comprise a nucleotide sequence that encodes one or more proteins selected from the group consisting of: cytokines, blood clotting factors, chemokines, costimulatory factors, transcription factors, hormones, growth factors and replacement genes. Examples of cytokines include IL-12, GM-CSF, and erythropoietin. Examples of blood clotting factors include Factor XIII and Factor IX. Examples of replacement genes include dystrophin (useful for treating muscular dystrophy) and CFPR (useful for treating cystic fibrosis). Examples of hormones include leptin. The nucleic acid molecule(s) may be provided as plasmid DNA. In some embodiments, the lamellar vesicles further comprise one or more proteins, polypeptides, peptides, or non-proteinaceous drugs/therapeutic compounds.

According to the invention, DNA or RNA that encodes an immunogen or physiologically active protein is introduced into the cells of tissue of an individual where it is expressed, thus producing the immunogen or physiologically active protein. The DNA or RNA sequences encoding the immunogen or physiologically active protein are linked to regulatory elements necessary for expression in the cells of the individual. Regulatory elements for DNA expression include a promoter and a polyadenylation signal. In addition, other elements, such as a Kozak region, may also be included in the genetic construct.

As used herein, the term "genetic construct" refers to the DNA or RNA molecules that comprise a nucleotide sequence which encodes the immunogen or physiologically active protein and which includes initiation and termination signals operably linked to regulatory elements including a promoter and polyadenylation signal capable of directing expression in the cells of the individual. In some embodiments, expressible forms of sequences that encode one or more immunogens and/or one or more physiologically active proteins are found on the same nucleic acid molecule that is delivered to the individual. In some embodiments, lamellar vesicles include two or more different species of nucleic acid molecules that include expressible forms of sequences that encode one or more different immunogens and/or one or more different physiologically active proteins to be delivered to the individual.

As used herein, the term "expressible form" refers to gene constructs which contain the necessary regulatory elements operably linked to a coding sequence that encodes an immunogen or physiologically active protein, such that when present in the cell of the individual, the coding sequence will be expressed.

Genetic constructs may comprise a nucleotide sequence that encodes an immunogen or physiologically active protein operably linked to regulatory elements needed for gene expression. When taken up by a cell, the genetic construct(s) may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal.

Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operably linked to the sequence that encodes the desired proteins and that the regulatory elements are operable in the individual to whom they are administered.

Initiation codons and a stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to: human promoters, viral promoters such as those from a herpes virus, a poxvirus, a papilloma, a parvovirus or a hepatitis virus; promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human elongation factor 1A, human Actin, human Myosin, human Hemoglobin, human muscle creatine and human metalothionein.

Examples of polyadenylation signals useful to practice the present invention, especially in the production of a genetic vaccine for humans, include but are not limited to bovine growth hormone polyadenylation signal, SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include a constitutive transport element from Mason-Pfizer monkey virus and/or enhancers. The enhancer may be selected from the group including but not limited to: human Actin, human Myosin, human Hemoglobin, human muscle creatine and viral enhancers such as those from CMV, RSV and EBV.

In order to maximize protein production, regulatory sequences may be selected which are well suited for gene expression in the cells into which the construct is administered. Moreover, codons may be selected which are most efficiently transcribed in the cell. One having ordinary skill in the art can produce DNA constructs which are functional in the cells.

The present invention may be used to immunize an individual against all pathogens such as viruses, prokaryotic and pathogenic eukaryotic organisms such as unicellular pathogenic organisms and multicellular parasites. The present invention is particularly useful to immunize an individual against those pathogens which infect cells such as viruses, and prokaryotes such as gonorrhea, listeria and shigella In addition, the present invention is also useful to immunize an individual against protozoan pathogens which include a stage in the life cycle where they are intracellular pathogens. As used herein, the term "intracellular pathogen" is meant to refer to a virus or pathogenic organism that, during at least part of its reproductive or life cycle, exists within a host cell and therein produces or causes to be produced, pathogen proteins. Table 1 provides a listing of some of the viral families and genera for which vaccines according to the present invention can be made. DNA constructs that comprise DNA sequences which encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2.

In order to produce a genetic vaccine to protect against pathogen infection, genetic material which encodes immunogenic proteins against which a protective immune response can be mounted must be included in a genetic construct as the coding sequence for the target. Whether the pathogen infects intracellularly, for which the present invention is particularly useful, or extracellularly, it is unlikely that all pathogen antigens will elicit a protective response. The present invention allows for vaccination with multiple pathogen antigens. The genetic construct used in the genetic vaccine can include genetic material which encodes many pathogen antigens. For example, several viral genes may be included in a single construct thereby providing multiple targets. Alternatively, multiple constructs that contain one or more pathogen genes can be included on different DNA molecules which are then combined and used to prepare vesicular complexes. Such vesicles contain two or more different DNA molecules with different gene constructs within a single vesicular structure.

Tables 1 and 2 include lists of some of the pathogenic agents and organisms for which genetic vaccines can be prepared to protect an individual from infection by them. In some preferred embodiments, the methods of immunizing an individual against a pathogen are directed against human immunodeficiency virus, HIV; human T cell leukemia virus, HTLV; influenza virus; hepatitis A virus; hepatitis B virus; hepatitis C virus; human papilloma virus, HPV; Herpes simplex 1 virus, HSV1; Herpes simplex 2 virus, HSV2; Cytomegalovirus, CMV; Epstein-Barr virus, EBR; rhinovirus; coronavirus; rotavirus; and respiratory syncytial virus.

Another aspect of the present invention provides a method of conferring a broad based protective immune response against hyperproliferating cells that are characteristic in hyperproliferative diseases and to a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer, such as lymphoma or melanoma, and psoriasis.

It has been discovered that introduction of a genetic construct that includes a nucleotide sequence which encodes an immunogenic "hyperproliferating cell"-associated protein into the cells of an individual results in the production of those proteins in the vaccinated cells of an individual. As used herein, the term "hyperproliferative-associated protein" is meant to refer to proteins that are associated with a hyperproliferative disease. To immunize against hyperproliferative diseases, a genetic construct that includes a nucleotide sequence which encodes a protein that is associated with a hyperproliferative disease is administered to an individual.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells. In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of antibodies would elicit an immune response including CTLs to eliminate those B cells that produce the antibody. In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

According to some preferred embodiments, the vesicle is a vaccine formulation and the DNA is plasmid DNA which operably encodes an immunogen against which an anti-pathogen immune response can be induced. Preferred embodiments include plasmids that encode immunogens which induce immune responses against pathogens set forth in Tables 1 and 2. According to some preferred embodiments, the immunogen is a pathogen antigen. In some embodiments, immunomodulating proteins may be included in the vesicle and/or encoded by the plasmid. In some preferred embodiments, immunogenic proteins and peptides, particularly those related to the immunogen encoded by the plasmid may be included in the vesicle.

According to some preferred embodiments, the DNA is plasmid DNA which operably encodes a therapeutically active protein such as an immunomodulating protein or an otherwise physiologically active protein. Delivery of such DNA to an individual results in expression of the protein which then is active in the individual.

In some embodiments of the invention, the nucleic acid molecules may be carrier DNA used to form the vesicular complexes to carry other active agents but not to encode proteins to be expressed in cells in the individual to whom the vesicular complexes are administered. Examples of carrier DNA include plasmid DNA, salmon sperm DNA, human DNA, bacterial DNA, and phage DNA. In some embodiments of the invention, the nucleic acid molecules may be RNA.

In some embodiments of the invention, the other active agent may be proteins polypeptides, peptides, RNAs, or other non-proteinaceous molecules such as therapeutical compounds/drugs. Examples of proteins include antigens/immunogens which are targets for a desired immune response, cytokines such as IL-12, GM-CSF, costimulatory factors, chemokines such as MCP-1 and RANTES, transcription factors, polymerases, hormones, and growth factors. Examples of RNAs include antisense RNA, ribozymes and triplex forming RNA. Examples of proteins, polypeptides and peptides include antigenic/immunogenic proteins, polypeptides and peptides which are targets for a desired immune response and biologically active peptides such as somatastatin and IGF-1. Examples of non-proteinaceous molecules such as therapeutical compounds/drugs include: anti-tumor compounds such as tamoxiphen, doxyrubicin, taxol, cis-platin; anti-viral compounds such as ddI and ddA, anti-inflammatory compounds such as NSAIDs and steroids; antibiotic compounds such as antifungal and antibacterial compounds, and cholesterol lowering drugs.

The local anesthetic/nucleic acid complex produces lamellar structures from the local anesthetics. The nucleic acid molecules interact with the hydrophilic portion of the local anesthetics while the lipophilic portion forms a membrane structure. Complex formation occurs under the specific conditions including specific molar ratios of local anesthetic and nucleic acid, specific salt concentrations and specific pH. Further, depending upon process steps, vesicles of different sizes can be produced having different macromolecular structures.

With regard to pH, the pH should be above the pKa of the local anesthetic to ensure that the amine group is positively charged. In preferred embodiments, the pH is 4–8.5, more preferably 6–7.5.

With regard to the salt concentration, the salt concentration should be sufficiently low to allow the positive charge of the local anesthetic complexes with the negative charge of the phosphate groups of the nucleic acid. In some embodiments, salt concentrations of local anesthetic/nucleic acid vesicle formulations are increased after complex formation. In preferred embodiments, salt concentration is 0–2M, more preferably 0–500 mM.

Routes of administration include parenteral as well as topical or mucosal routes. In some embodiments, the vesicles are delivered intramuscularly, intravenously, intraarterially, intratumor, intradermally, subcutaneously, transdermally, intraperatoneally, topically, intranasally, orally including enterically protected oral delivery, by inhalation, or topically or by lavage to mucosal tissue selected from the group consisting of vaginal, rectal, urethral, buccal and sublingual. Composition of the invention may be administered by means including, but not limited to, traditional syringes, needleless injection devices, or "microprojectile bombardment gene guns". Microprojectile particle bombardment procedures taught by Sanford et al. in U.S Pat. No. 4,945,050 issued Jul. 31, 1990, which is incorporated herein by reference, may be adapted for administration of compositions of the invention into individuals.

As used herein, the terms "pharmaceutical compositions" and "injectable pharmaceutical compositions" are intended to have their ordinary and well understood and accepted meanings which are fully appreciated by those with ordinary skill in the art. Compositions which are administered to patients as pharmaceutical compositions are generally sterile, pyrogen free compositions. Pharmaceutical compositions suitable for injection, i.e. injectable pharinaceutical compositions, are sterile, pyrogen free and essentially free of foreign matter, as well as adjusted for isotonicity and pH appropriate and consistent with safe and effective injection into an individual.

With regard to the local anesthetic/nucleic acid ratio, the size of the particle complex is dependent upon the ratio. Thus, particle size can determined by adjusting the local anesthetic/nucleic acid ratio. Different particle sizes may be desired depending upon what cell type is targeted for gene transfer.

The size of the local anesthetic/nucleic acid vesicles or the higher order structures can be controlled by several factors, including if long chain fatty acid type lipids are used, the hydrophobic chain length on both the lipid and the local anesthetic components, and the exact ratios of local anesthetics and lipids to each other. Furthermore, for vesicles used for nucleic acid delivery, the ratio of concentration of local anesthetic or concentration of local anesthetic and cationic lipid to concentration of nucleic acid is important to the size and structure of the particle. Variation of the particle size (from 10 nm to 100 $\mu$g diameter as measured by scanning electron microscopy) would result in different tissue distribution and distribution kinetics, which might also be influenced by mode/method of particle injection or delivery. For example, particles of 50–200 nm diameter as measured by scanning electron microscopy injected intravenous might preferentially be taken up by liver hepatocytes. Particles of 0.1–10 $\mu$m injected intravenous, intramuscular, subcutaneous or intradermal might preferentially be taken up by phagocytic cells such as Kupfer cells, and/or immune system cells such as various types of dendritic cells, including Langerhahn cells, and macrophages. Particles of various sizes (50 nm–100 $\mu$m diameter as measured by scanning electron microscopy) might be taken up via transdermal delivery techniques, or via topical application to skin or mucosal surfaces, or via oral delivery alone or in combination with other ingredients in tablets, capsules, etc.

In some preferred embodiments, local anesthetics are provided at a final concentration of 0.01–2.5% (w/v), more preferably 0.05–1.25% (w/v). In some preferred embodiments, the final concentration is 0.25% (w/v).

In some preferred embodiments, nucleic acids are provided at a final concentration of 1 $\mu$g/ml–10 mg/ml, more preferably 100 $\mu$g/ml–3 $\mu$g/ml. In some preferred embodiments, the final concentration is 1 mg/ml.

In some preferred embodiments, the [nucleic acid]:[local anesthetic] concentration ratio is [1 $\mu$g/ml–10 mg/ml]: [0.01–2.5% (w/v)], preferably [100 $\mu$g/ml–3 mg/ml]: [0.05–1.25% (w/v)]. In some preferred embodiments, the [nucleic acid]:[local anesthetic] concentration ratio is [800 $\mu$g/ml–1000 $\mu$g/ml]:[0.1–0.25% (w/v)].

Local anesthetic vesicles form spontaneously when combined with nucleic acid molecules. The charge of the local anesthetic can be determined by selecting conditions that favor a charged form. In some preferred embodiments, the local anesthetic is positively charged and combined with negatively charged nucleic acid, in some preferred embodiments DNA. Combining positively charged local anesthetics with DNA results in formation of vesicle structures. Individual vesicle structures may aggregate into larger, higher order structures. Some aggregates appear as rod-like structures which appear to be individual vesicle structures organized as peas in a pod, i.e vesicles encapsulated in a larger lamellar vesicle structure.

If the local anesthetic, such as bupivacaine, is directly mixed with the nucleic acid, such as DNA, such as by immediate mixture, vesicle structures of about 100–150 nm diameter as measured by scanning electron microscopy form which can aggregate into larger, and in some cases, irregular-shaped structures that are greater than 300 nm diameter as measured by scanning electron microscopy. Slowing rates of mixing can be obtained using dialysis; either by dialyzing local anesthetic into a nucleic acid molecule solution or by combining local anesthetic, nucleic acid molecules and salt and removing the salt be dialysis. Combining the local anesthetic and nucleic acid by slow rate of mixing such as by dialysis using low concentrations of DNA relative to concentration of local anesthetic favors formation of smaller structures of 50–150 nm diameter as measured by scanning electron microscopy. Combining the local anesthetic and nucleic acid using higher concentrations of DNA relative to concentration of local anesthetic favors formation of larger structures up to 1 micron or greater in diameter as measured by scanning electron microscopy. A preferred slow mixing procedure combines the components in the presence of high salt which is removed by dialysis over several hours. As the salt is removed, the conditions move toward self assembly and vesicle structures form.

As set forth above, dialysis may be used to control the rate of vesicle formation. In some processes, the local anesthetic and nucleic acid molecules are combined in a dialysis membrane in a solution with high salt concentration. The membrane is then placed in a vessel that contains a low salt concentration, usually the concentration desired for the final, vesicle containing solution. The salt in the solution in the membrane migrates through and out of the membrane into the surrounding solution and the salt concentration in the membrane is reduced accordingly. As the salt concentration decreases, the solution within the membrane favors vesicle formation. This process is particularly useful when additional agents to be encapsulated in the vesicles are hydrophobic.

In some processes, the nucleic acid molecules are in a solution in a dialysis membrane. The membrane is then placed in a vessel that contains local anesthetic at the concentration for vesicle formation, usually the final concentration of the vesicle-containing solution. The local anesthetic in the surrounding solution migrates through the membrane into the solution in the membrane. As the local anesthetic concentration in the solution in the membrane increases, the solution within the membrane favors vesicle formation. Generally, using a dialysis membrane with a size cut off of 10,000–100,000 kD, equilibration time for the local anesthetic concentration inside of the membrane to become equal to the local anesthetic concentration outside of the membrane is about 2–3 hours. Using a dialysis membrane with a size cut off of 3,000 kD, equilibration time for the local anesthetic concentration inside of the membrane to become equal to the local anesthetic concentration outside of the membrane is about 5 hours. Additional agents to be encapsulated in the vesicle may be included in the nucleic acid solution within the membrane provided such agents are soluble in the solution.

In one embodiment, bupivacaine is combined at a final concentration of 0.25% (w/v) bupivacaine in an aqueous solution with 100–1000 µg/ml DNA by direct mixing. The pH is below 8, preferably 6.5–7. The salt concentration is less than 200 mM. Vesicle structures of about 100–150 nm diameter as measured by scanning electron microscopy are formed as are aggregates of such vesicles which form larger structures that are greater than 300 mn diameter as measured by scanning electron microscopy.

In one embodiment, bupivacaine is combined at a final concentration of 0.25% (w/v) with an organic solvent such as chloroform and dried by evaporation. DNA in aqueous solution at 100–1000 µg/ml is mixed with evaporate. The pH is below 8, preferably 6.5–7. The salt concentration is less than 500 mM. Vesicle structures of about 100–150 nm diameter as measured by scanning electron microscopy are formed as are aggregates of such vesicles which form larger structures that are greater than 300 nm diameter as measured by scanning electron microscopy.

In one embodiment, bupivacaine is combined at a final concentration of 0.25% (w/v) bupivacaine in an aqueous solution with less than 100 µg/ml DNA. The pH is below 8, preferably 6.5–7. The salt concentration is less than 500 mM. Vesicle structures of about 50–150 nm diameter as measured by scanning electron microscopy are formed.

In one embodiment, bupivacaine is combined at a final concentration of 0.25% (w/v) bupivacaine in an aqueous solution with up to 1000 µg/ml DNA. The two materials are combined slowly by dialysis over greater than one hour. The pH is below 8, preferably 6.5–7. The salt concentration is above 2M. The salt is extracted out of the solution and vesicles self assemble as the salt is removed. Vesicle structures of about 50–150 nm diameter as measured by scanning electron microscopy are formed. Cations such as $Ca^{++}$ or anions such as $PO_4$ may be used to stabilize the final structure.

In another embodiment, a mixture of local anesthetic, lipid, and nucleic acid in high salt slowly self assembles into vesicles upon dialysis.

In one embodiment, local anesthetic and, optionally, lipids are mixed in an organic solvent as described above. The solvent is evaporated by standard techniques. An aqueous buffer containing the nucleic acid molecule is added to the dried material, and vesicles self-assemble upon mixing. For delivery of hydrophobic active agents, the active agent can be added to the lipids in solvent prior to drying. Proteins, polypeptide, peptides and non-proteinaceous, hydrophilic compounds can be included in buffer that contains the nucleic acid molecule. Active agents can be encapsulated accordingly.

In another embodiment, cationic vesicles can be made as set forth above except they are formed without nucleic acid molecules which are added afterwards. For example, local anesthetic and, optionally, lipids are mixed in an organic solvent as described above. The solvent is evaporated by standard techniques. An aqueous buffer that does not contain the nucleic acid molecule is added to the dried material, and "empty" vesicles self-assemble upon mixing. The buffer containing nucleic acid molecule is then added in solution as a second step after reconstitution. This is particularly useful for a nucleic acid, which might result in a larger, higher order particulate multi-lamellae structure.

In another example, solid vesicles which precipitate as particles or crystals. in association with the nucleic acid, are produced in mixture by adjusting pH upward toward the pKa of the local anesthetic.

In some embodiments, local anesthetic:nucleic acid vesicles further comprise proteins such as cytokines and/or immunogenic proteins or peptides. Accordingly, immunomodulating proteins can be administered as part of local anesthetic:nucleic acid complexes in which the nucleic acid encodes an immunomodulating protein and/or an immunogenic protein. In some embodiments, the nucleic acid is a genetic vaccine and the co-agent protein is an immunomodulating protein such as a cytokine, for example GMCSF or L-12. In some embodiments, the nucleic acid is a genetic vaccine and the co-agent protein is an immunogenic protein or peptide. According to such embodiments, the vaccine as delivered is a simultaneous prime/boost dose.

Vesicles can combine to form larger structure/complexes including structures 1–5 microns.

In some embodiments, the vesicles are greater than 400 nm diameter as measured by scanning electron microscopy. Such vesicles can be used to deliver material to the lung when administered to an individual, for example, by intravenous administration.

The compositions and methods of the present invention are useful in the fields of both human and veterinary medicine. Accordingly, the compositions and methods of the present invention can be used to therapeutically and prophylactically treat individual mammals, birds or fish. The compositions and methods of the present invention can be particularly useful for compositions and methods of treating individuals of mammalian species including human, bovine, ovine, porcine, equine, canine and feline species.

The present invention is not intended to be limited by any particular theory. The Examples set out below refer to some embodiments of aspects of the present invention. The Examples are not meant to limit the scope of the invention but rather serve exemplary purposes. One having ordinary skill in the art can readily appreciate additional aspects and embodiments of the invention.

EXAMPLES

According to some preferred embodiments of the present invention, immune responses induced by local anesthetic facilitated DNA vaccines can be improved when local anesthetic and DNA are combined and delivered as local anesthetic vesicles with DNA. In some preferred embodiments, the local anesthetic is bupivacaine.

According to the present invention, immune responses induced by local anesthetic facilitated DNA vaccines can be improved when a local anesthetic is combined with a co-agent and DNA to form vesicles.

An anionic molecule such as DNA associates with the positive, hydrophilic portion of the self-assembled structure. The complex associates with cells and its highly lipophilic property facilitate uptake into cells. Utility includes gene therapy and genetic immunization.

In some embodiments, larger vesicles are generated which are sufficient in size to be taken up by cells as particulates by a mechanism involving pino- or phagocytosis. Such large particulate vesicles are used in the vaccine field for immunization or immunotherapy or in the gene therapy field for targeting of cells in the immune system, such as MHC-II expressing antigen presenting cells like dendritic cells or macrophages. The additional advantage of such a large complex is that the local anesthetic also facilitates release from endosomes and lysozomes within cells.

In some embodiments, lyophilized/desiccated local anesthetic/DNA vesicles have utility for gene delivery and genetic immunization. As an example, they are used alone or in combination with other solid ingredients for making tablets for oral DNA delivery, or for making nanoparticles or microparticles for DNA delivery. Local anesthetic complexes or particles are used for oral delivery of vaccines or for gene therapy, since they protect the associated active molecules from degradation within the stomach and facilitate uptake into gut-associated lymphatic tissues.

In another example, a hydrophobic, poorly soluble drug is encapsulated within the hydrophobic environment at the core of the vesicle, while the surface of the structure is positively charged which improves solubility of the drug. Positive-charged species have a natural attraction for the phospholipid-rich, negative-charged surface of cells. After attraction, the highly lipophilic nature of the structure facilitates delivery through cell membranes. Utility includes delivery of poorly soluble or systemically toxic cancer drugs such as taxols or vincristine to breast cancer cells/tumors.

In another example, the vesicles protect associated biomolecules from enzymatic degradation in blood, or from non-productive interaction with blood components, or from non-productive immune responses. Amide-type local anesthetics used in these complexes may have a particular advantage over ester-type local anesthetics since they are not degraded in blood.

In another example, vesicles are formulated in a cream, jelly, lotion, ointment for topical delivery of drugs, DNA, etc. to mucosal sites and through skin.

TABLE 1

| | |
|---|---|
| Picornavirus Family | |
| Genera: | Rhinoviruses: (Medical) responsible for ~50% cases of the common cold. |
| | Enteroviruses: (Medical) includes polioviruses, Coxsackieviruses, echoviruses, and human enteroviruses such as hepatitis A virus. |
| | Apthoviruses: (Veterinary) these are the foot and mouth disease viruses. |
| Target antigens: | VP1, VP2, VP3, VP4, VPG |
| Calcivirus Family | |
| Genera: | Norwalk Group of Viruses: (Medical) these viruses are an important causative agent of epidemic gastroenteritis. |
| Togavirus Family | |
| Genera: | Alphaviruses: (Medical and Veterinary) examples include Sindbis viruses, RossRiver virus and Eastern & Western Equine encephalitis. |
| | Rubivirus: (Medical) Rubella virus. |
| Flariviridue Family | Examples include: (Medical) dengue, yellow fever, Japanese encephalitis, St. Louis encephalitis and tick borne encephalitis viruses. |
| Hepatitis C Virus: | (Medical) these viruses are not placed in a family yet but are believed to be either a togavirus or a flavivirus. Most similarity is with togavirus family. |
| Coronavirus Family: | (Medical and Veterinary) |
| | Infectious bronchitis virus (poultry) |
| | Porcine transmissible gastroenteric virus (pig) |
| | Porcine hemagglutinating encephalomyelitis virus (pig) |
| | Feline infectious peritonitis virus (cats) |
| | Feline enteric coronavirus (cat) |
| | Canine coronavirus (dog) |

TABLE 1-continued

| | |
|---|---|
| Target antigens: | The human respiratory coronaviruses cause ~40 cases of common cold. EX. 224E, 0C43<br>Note - coronaviruses may cause non-A, B or C hepatitis<br>E1 - also called M or matrix protein<br>E2 - also called S or Spike protein<br>E3 - also called HE or hemagglutin-elterose glycoprotein (not present in all coronaviruses)<br>N - nucleocapsid |
| Rhabdovirus Family | |
| Genera: | Vesiculovirus: Vesicular Stomatitis Virus<br>Lyssavirus: (medical and veterinary) rabies |
| Target antigens: | G protein<br>N protein |
| Filoviridue Family: | (Medical)<br>Hemorrhagic fever viruses such as Marburg and Ebola virus |
| Paramyxovirus Family: | |
| Genera: | Parainfluenza Virus Type 1<br>Parainfluenza Virus Type 3<br>Bovine Parainfluenza Virus Type 3<br>Rubulavirus: (Medical and Veterinary)<br>Mumps virus, Parainfluenza Virus Type 2, Parainfluenza Virus Type 4, NewCastle disease virus (important pathogen in chickens)<br>Morbillivirus: (Medical and Veterinary)<br>Measles, canine distemper<br>Pneumonvirus: (Medical and Veterinary)<br>Respiratory syncytial virus |
| Orthomyxovirus Family | (Medical)<br>The Influenza virus |
| Bunyavirus Family | |
| Genera: | Bunyavirus: (Medical) California encephalitis, La Crosse<br>Phlebovirus: (Medical) Rift Valley Fever<br>Hantavirus: Puremala is a hemahagin fever virus<br>Nairovirus (Veterinary) Nairobi sheep disease<br>Also many unassigned bungaviruses |
| Arenavirus Family | (Medical)<br>LCM, Lassa fever virus |
| Reovirus Family | |
| Genera: | Reovirus: a possible human pathogen<br>Rotavirus: acute gastroenteritis in children<br>Orbiviruses: (Medical and Veterinary)<br>Cultivirus: Colorado Tick fever, Lebombo (humans) equine encephalosis, blue tongue |
| Retrovirus Family | |
| Sub-Family: | Oncorivirinal: (Veterinary) (Medical) feline leukemia virus, HTLVI and HTLVII<br>Lentivirinal: (Medical and Veterinary) HIV, feline immunodeficiency virus, equine infections, anemia virus<br>Spumavirinal |
| Papovavirus Family | |
| Sub-Family: | Polyomaviruses: (Medical) BKU and JCU viruses |
| Sub-Family: | Papillomavirus: (Medical) many viral types associated with cancers or malignant progression of papilloma |
| Adenovirus | (Medical)<br>EX AD7, ARD., O.B. - cause respiratory disease - some adenoviruses such as 275 cause enteritis |
| Parvovirus Family | (Veterinary)<br>Feline parvovirus: causes feline enteritis<br>Feline panleucopeniavirus<br>Canine parvovirus<br>Porcine parvovirus |
| Herpesvirus Family | |
| Sub-Family: | alphaherpesviridue |
| Genera: | Simplexvirus (Medical)<br>HSVI, HSVII<br>Varicellovirus: (Medical - Veterinary) pseudorabies - varicella zoster |
| Sub-Family - | betaherpesviridue |
| Genera: | Cytomegalovirus (Medical)<br>HCMV<br>Muromegalovirus |
| Sub-Family: | Gammaherpesviridue |

TABLE 1-continued

Genera: Lymphocryptovirus (Medical)
EBV - (Burkitts lympho)
Rhadinovirus

Poxvirus Family

Sub-Family: Chordopoxviridue (Medical - Veterinary)
Genera: Orthopoxvirus
Variola (Smallpox)
Vaccinia (Cowpox)
Parapoxivirus - Veterinary
Auipoxvirus - Veterinary
Capripoxvirus
Leporipoxvirus
Suipoxvirus
Sub-Family: Entemopoxviridue
Hepadnavirus Family: Hepatitis B virus
Unclassified: Hepatitis delta virus

TABLE 2

Bacterial pathogens

Pathogenic gram-positive cocci include: pneumococcal; staphylococcal; and streptococcal. Pathogenic gram-negative cocci include: meningococcal; and gonococcal.
Pathogenic enteric gram-negative bacilli include: enterobacteriaceae; pseudomonas, acinetobacteria and eikenella; melioidosis; salmonella; shigellosis; hemophilus; moraxella; chancroid; brucellosis; tularemia; yersinia (pasteurella); streptobacillus moniliformis and spirillum; listeria monocytogenes; erysipelothrix rhusiopathiae; diphtheria; cholera; anthrax; donovanosis (granuloma inguinale); and bartonellosis.
Pathogenic anaerobic bacteria include: tetanus; botulism; other clostridia; tuberculosis; leprosy; and other mycobacteria. Pathogenic spirochetal diseases include: syphilis; treponematoses: yaws, pinta and endemic syphilis; and leptospirosis.
Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis.
Rickettsial infections include rickettsial and rickettsioses.
Examples of mycoplasma and chlamydial infections include: mycoplasma pneumoniae; lymphogranuloma venereum; psittacosis; and perinatal chlamydial infections.

Pathogenic eukaryotes

Pathogenic protozoans and helminths and infections thereby include: amebiasis; malaria; leishmaniasis; trypanosomiasis; toxoplasmosis; pneumocystis carinii; babesiosis; giardiasis; trichinosis; filariasis; schistosomiasis; nematodes; trematodes or flukes; and cestode (tapeworm) infections.

What is claimed is:

1. A method of delivering a nucleic acid molecule to a cell comprising the step of delivering to said cell a composition comprising lamellar vesicles, wherein said lamellar vesicles comprise a local anesthetic and nucleic acid molecules selected from the group consisting of: a nucleic acid molecule that comprises a nucleotide sequence that encodes a product selected from the group consisting of an antisense oligonucleotide, a ribozyme and a triplex forming nucleic acid molecule.

2. The method according to claim 1 wherein the proportion of local anesthetic to nucleic acid in the composition is 0.01 to 2.5% w/v local anesthetic to 1 µg/ml to 10 mg/ml nucleic acid.

3. The method according to claim 1 wherein the proportion of local anesthetic to nucleic acid in the composition is 0.05 to 1.25% w/v local anesthetic to 100 µg/ml to 1 mg/ml nucleic acid.

4. The method according to claim 1 wherein the proportion of local anesthetic to nucleic acid in the composition is 0.1 to 0.5% w/v local anesthetic to 500 µg/ml to 1500 µg/ml nucleic acid.

5. The method according to claim 1 wherein said lamellar vesicles are 50 to 150 nm in diameter.

6. The method according to claim 1 wherein greater than 50% of said lamellar vesicles are greater than 300 nm in diameter.

7. The method according to claim 1 wherein greater than 50% of said lamellar vesicles are less than 400 nm in diameter.

8. The method according to claim 1 wherein said lamellar vesicles consist of the local anesthetic bupivacaine and nucleic acid molecules.

9. The method according to claim 8, wherein the lamellar vesicles are formed by mixing 0.25% w/v bupivacaine with the nucleic acid molecules.

10. The method according to claim 1 wherein said nucleic acid molecule is DNA.

11. The method according to claim 1 wherein said nucleic acid molecule is plasmid DNA.

12. The method according to claim 1 wherein said lamellar vesicles further comprise one or more compounds selected from the group consisting of: cationic lipids, neutral lipids, anionic lipids, cationic surfactants, neutral surfactants, anionic surfactants, cationic detergents, neutral detergents, and anionic detergents.

13. The method according to claim 1, wherein the lamellar vesicles are formed by mixing bupivacaine with a DNA molecule at a pH of 6.5 to 7.

14. A composition comprising lamellar vesicles and a physiologically acceptable carrier or diluent, wherein said lamellar vesicles comprise a local anaesthetic and a protein, polypeptide, peptide, or non-proteinaceous compound.

15. The composition of claim 14 wherein said composition is an injectable pharmaceutical composition.

16. The composition according to claim 14, wherein said local anaesthetic is bupivacaine.

17. The composition according to claim 14, wherein said local anesthetic is bupivacaine.

18. The composition according to claim 14, wherein the proportion of local anesthetic to nucleic acid in the lamellar vesicles is 0.05 w/v to 1.25% w/v bupivacaine to 100 µg/ml to 1 mg/ml nucleic acid.

19. The composition according to claim 18, wherein the lamellar vesicles comprise 0.1 w/v to 0.5 w/v bupivacaine to 500 µg/ml to 1500 µg/ml nucleic acid.

20. The composition according to claim 14, wherein the lamellar vesicles are 50 to 150 nm in diameter.

21. The composition according to claim 14, wherein greater than 50% of the lamellar vesicles are greater than 300 nm in diameter.

22. The composition according to claim 14, wherein greater than 50% of the lamellar vesicles are less than 400 nm in diameter.

23. A method of delivering a protein to a cell comprising the step of delivering to said cell a composition comprising lamellar vesicles, wherein said lamellar vesicles comprise a local anesthetic and nucleic acid molecules that comprise a nucleotide sequence that encodes a protein operably linked to regulatory sequences, wherein said nucleic acid molecules are taken up by said cell and express said protein in said cell, wherein said delivering step is performed in vitro.

24. A method of delivering a nucleic acid molecule to a cell comprising the step of delivering to said cell a composition comprising lamellar vesicles, wherein said lamellar vesicles comprise a local anesthetic and nucleic acid molecules selected from the group consisting of: a nucleic acid molecule that comprises a nucleotide sequence that encodes a product selected from the group consisting of an antisense oligonucleotide, a ribozyme and a triplex forming nucleic acid molecule, wherein said delivering step is performed in vitro.

25. A method of inducing an immune response against a protein comprising the step of delivering a composition comprising lamellar vesicles to individual, wherein said lamellar vesicles comprise 0.01 to 2.5 % w/v bupivacaine and 1 µg/ml to 10 mg/ml nucleic acid molecules encoding a product which is expressed in the individual, thereby inducing an immune response to the product.

26. The method according to claim 25, wherein said lamellar vesicles comprises a nucleic acid molecule comprising a nucleotide sequence encoding a protein operably linked to regulatory sequences, wherein said nucleic acid molecule is taken up by said cell and permits expression of said protein in said cell, thereby inducing an immune response to said protein.

27. The method according to claim 25, wherein said lamellar vesicles comprise a nucleic acid molecule that comprises a nucleotide sequence that encodes a product selected from the group consisting of an antisense oligonucleotide, a ribozyme and a triplex forming nucleic acid molecule.

28. The method according to claim 25, wherein the lamellar vesicles comprise 0.05 w/v to 1.25% w/v bupivacaine to 100 µg/ml to 1 mg/ml nucleic acid.

29. The method according to claim 28, wherein the lamellar vesicles comprise 0.1 w/v to 0.5 w/v bupivacaine to 500 µg/ml to 1500 µg/ml nucleic acid.

30. The method according to claim 25, wherein the lamellar vesicles are 50 to 150 nm in diameter.

31. The method according to claim 25, wherein greater than 50% of the lamellar vesicles are greater than 300 nm in diameter.

32. The method according to claim 25, wherein greater than 50% of the lamellar vesicles are less than 400 nm in diameter.

33. A method of inducing an immune response against a protein, peptide or polypeptide comprising the step of delivering to an individual a composition comprising lamellar vesicles, wherein said lamellar vesicles comprise a local anesthetic and nucleic acid molecules that comprise a nucleotide sequence that encodes a product selected from the group consisting of a protein, peptide and polypeptide operably linked to regulatory sequences, wherein said nucleic acid molecules are taken up by said cell and express said product in said cell, thereby inducing an immune response to said product.

34. The method according to claim 33 wherein the proportion of local anesthetic to nucleic acid in the lamellar vesicles is 0.01 to 2.5% w/v local anesthetic to 1 µg/ml to 10 mg/ml nucleic acid.

35. The method according to claim 33 wherein the proportion of local anesthetic to nucleic acid in the lamellar vesicles is 0.05 to 1.25% w/v local anesthetic to 100 µg/ml to 1 mg/ml nucleic acid.

36. The method according to claim 33 wherein the proportion of local anesthetic to nucleic acid in the lamellar vesicles is 0.1 to 0.5% w/v local anesthetic to 500 µg/ml to 1500 µg/ml nucleic acid.

37. The method according to claim 33 wherein said lamellar vesicles are 50 to 150 nm in diameter.

38. The method according to claim 33 wherein greater than 50% of said lamellar vesicles are greater than 300 nm in diameter.

39. The method according to claim 33 wherein greater than 50% of said lamellar vesicles are less than 400 nm in diameter.

40. The method according to claim 33 wherein said local anesthetic is bupivacaine.

41. The method according to claim 33 wherein said nucleic acid molecule is DNA.

42. The method according to claim 33 wherein said nucleic acid molecule is plasmid DNA.

43. The method according to claim 33 wherein said lamellar vesicles further comprise one or more compounds selected from the group consisting of: cationic lipids, neutral lipids, anionic lipids, cationic surfactants, neutral surfactants, anionic surfactants, cationic detergents, neutral detergents, and anionic detergents.

44. The method according to claim 33 wherein said lamellar vesicles further comprise one or more compounds selected from the group consisting of: proteins, polypeptides, peptides, and non-proteinaceous compound.

45. The method according to claim 33 wherein said lamellar vesicles further comprise an immunogenic protein or peptide.

46. The method according to claim 33 wherein said lamellar vesicles further comprise a biologically active protein selected from the group consisting of: cytokines, costimulatory factors, transcription factors, hormones, and growth factors.

47. The method according to claim 33 wherein said lamellar vesicles further comprise a non-proteinaceous compound.

48. The method according to claim 40, wherein the lamellar vesicles are formed by mixing 0.25% w/v bupivacaine with a DNA molecule.

49. The method according to claim 33, wherein the lamellar vesicles consist of the local anesthetic bupivacaine and nucleic acid molecules.

50. The method according to claim 49, wherein the bupivacaine is present in an amount of 0.25% w/v of the lamellar vesicle.

51. The method according to claim 33, wherein the lamellar vesicles are formed by mixing bupivacaine with a DNA molecule at a pH of 6.5 to 7.

* * * * *

UNITED STATES PATENT AND TRADEMARK OFFICE
CERTIFICATE OF CORRECTION

PATENT NO. : 6,383,512 B1
DATED : May 7, 2002
INVENTOR(S) : Richard Ciccarelli et al.

It is certified that error appears in the above-identified patent and that said Letters Patent is hereby corrected as shown below:

Column 2,
Line 7, replace "drugsltherapeutic" with -- drugs/therapeutic --.

Column 10,
Line 13, replace "shigella In" with -- shigella. In --.

Column 13,
Line 46, replace "pharinaceitical" with -- pharmaceutical --.

Column 22,
Lines 57 and 58, delete claim 17

Signed and Sealed this

Twenty-ninth Day of April, 2003

JAMES E. ROGAN
*Director of the United States Patent and Trademark Office*